(12) United States Patent
Tebbe (10) Patent No.: US 6,709,673 B1
(45) Date of Patent: Mar. 23, 2004

(54) MICROCAPSULE SYSTEM FOR ENVIRONMENT-INDUCED RELEASE OF ACTIVE AGENTS

(75) Inventor: Gerold Tebbe, Monte Carlo (MC)

(73) Assignee: Deotexis Inc., New York, NY (US)

( * ) Notice: Subject to any disclaimer, the term of this patent is extended or adjusted under 35 U.S.C. 154(b) by 0 days.

(21) Appl. No.: 09/704,950

(22) Filed: Nov. 2, 2000

(30) Foreign Application Priority Data

Nov. 2, 1999 (DE) .......................................... 199 52 586

(51) Int. Cl.[7] .............................. A61K 9/48; A61K 9/54
(52) U.S. Cl. ........................................ 424/451; 424/458
(58) Field of Search ................................. 424/451, 458

(56) References Cited

U.S. PATENT DOCUMENTS

| | | | | |
|---|---|---|---|---|
| 5,026,559 A | * | 6/1991 | Eichel et al. ............... | 424/458 |
| 5,422,120 A | * | 6/1995 | Kim ........................... | 424/450 |
| 5,545,423 A | * | 8/1996 | Soon-Shiong et al. ...... | 424/484 |
| 6,495,161 B1 | * | 12/2002 | Soon-Shiong et al. ...... | 424/451 |

FOREIGN PATENT DOCUMENTS

DE   40 00 920 A1   7/1991

OTHER PUBLICATIONS

Hanson, GR. Analgesic, Antipyretic and Anti-inflammatory Drugs Remington: the Science and Practice of Pharmacy Chapter 72, p. 1211 1995.*

* cited by examiner

*Primary Examiner*—Thurman K. Page
*Assistant Examiner*—S. Tran
(74) *Attorney, Agent, or Firm*—Factor & Lake (57) ABSTRACT

A microcapsule system is used to store active agents and release them as a function of specific environmental parameters. The active agents are contained in capsules having a capsule wall comprising an environment-induced material. To allow sequential, time-controlled release of the active agents, provision is made for a plurality of capsules to be accommodated in at least one outer capsule, thereby forming an inner encapsulation layer, wherein the outer capsules form an outer encapsulation layer. Like the capsule wall of the inner capsules, the capsule wall of the outer capsule is made of an environment-induced material.

8 Claims, 10 Drawing Sheets

MICROCAPSULE SYSTEM FOR ENVIRONMENT-INDUCED RELEASE OF ACTIVE AGENTS

FIELD OF THE INVENTION

The present invention relates to a microcapsule system for environment-induced release of active agents.

BACKGROUND ART

"Environment-induced" is understood to mean, here and below, that the walls of the capsules of the microcapsule system comprise a material which becomes unstable under the influence of one or more specific environmental parameters, such that the corresponding capsules become permeable or burst open and release the active agent optionally contained therein. Examples of such environmental parameters are pressure, temperature, deformation, light and other electromagnetic radiation, particulate radiation, chemical substances etc. Time should also be viewed as an environmental parameter for the purposes of the invention.

Such a microcapsule system is known from DE 40 00 920 A1, for example. In said patent, microcapsules filled with skin care oil are applied to the surface of a cloth. In this way, the skin care oil is protected against evaporation during storage of the cloth. If the cloth is rubbed against the skin, for example, the capsule walls burst as a result of deformation, such that the skin care oil contained in the capsules is released into the surrounding area and may perform its action on the skin of the user.

However, in many instances of use, it may be desirable for not all the active agents to be released at once, but for release of the active agents from the respective microcapsules to proceed in a specific sequence over time.

BRIEF SUMMARY OF THE INVENTION

This object is achieved by a microcapsule system for environment-induced release of active agents, comprising a plurality of capsules having a capsule wall comprising an environment-induced material, an active agent being contained in at least some of the capsules, wherein the plurality of capsules are accommodated in at least one outer capsule and thus form an inner encapsulation layer and the capsule wall of the outer capsule likewise comprises an environment-induced material and the outer capsule forms an outer encapsulation layer.

Through the "encapsulation" provided according to the invention of inner capsules in at least one outer capsule, it is possible to achieve sequential release of the active agents, i.e. release occurring in stages over time. The active agents stored in the microcapsule system are thus not necessarily released at once from the respective microcapsules, but rather in a freely selectable sequence over time. This opens up numerous new possibilities, precisely adaptable to the respective requirements, for use of the microcapsule system according to the invention.

Advantageous modifications of the invention are indicated in subclaims.

A modification of the invention increases the number of possible stages over time. The number of possible encapsulation stages is limited only by the maximum possible size of the capsules of the outermost encapsulation layer, which may vary from one application to another.

It is possible to release relatively large amounts of active agent from an encapsulation layer at the same time when said encapsulation layer is broken open.

Complex release sequences for the active agents contained in the capsules of an encapsulation layer may be achieved by two modifications of the invention.

In many instances, it is desirable to release not the same but different active agents in sequence.

The encapsulation layers can be broken open from the outside inwards. The active agents are thus not merely released from the corresponding capsules in sequence, but also discharged into the surrounding area in sequence.

In a modification of the invention, breaking open proceeds in the opposite direction, i.e. from the inside outwards. This is particularly advantageous if, for example, different active agents are firstly to be mixed together before the outermost encapsulation layer is broken open and the active agent mixture thus produced is released to the surrounding area.

BRIEF DESCRIPTION OF THE DRAWINGS

The invention is described in more detail below with the aid of two exemplary embodiments and with reference to the drawings, in which.

DETAILED DESCRIPTION OF THE PREFERRED EMBODIMENTS

Figure 1:
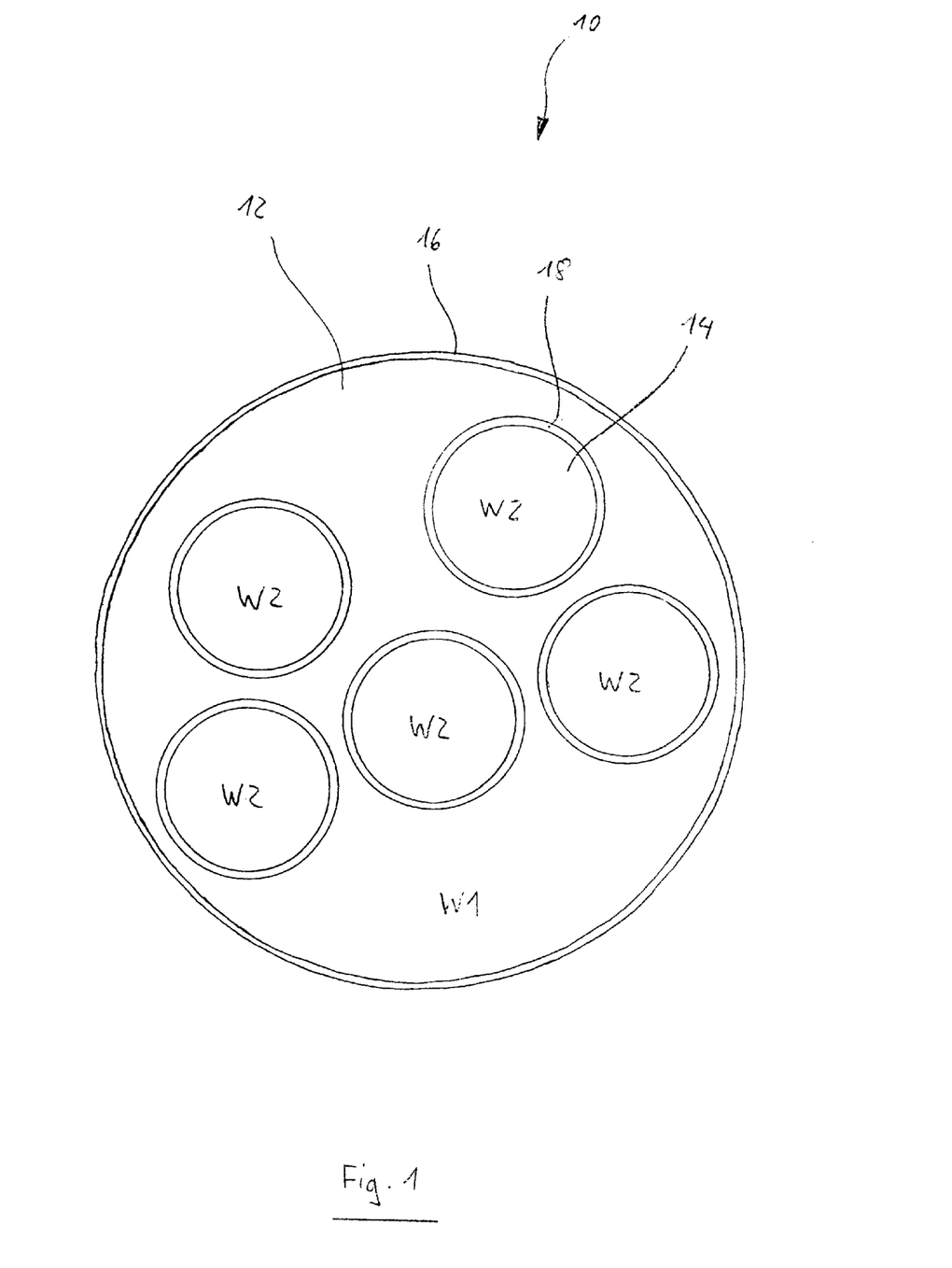
FIG. 1: shows a greatly enlarged section through a first exemplary embodiment of a microcapsule system.
Figure 2:
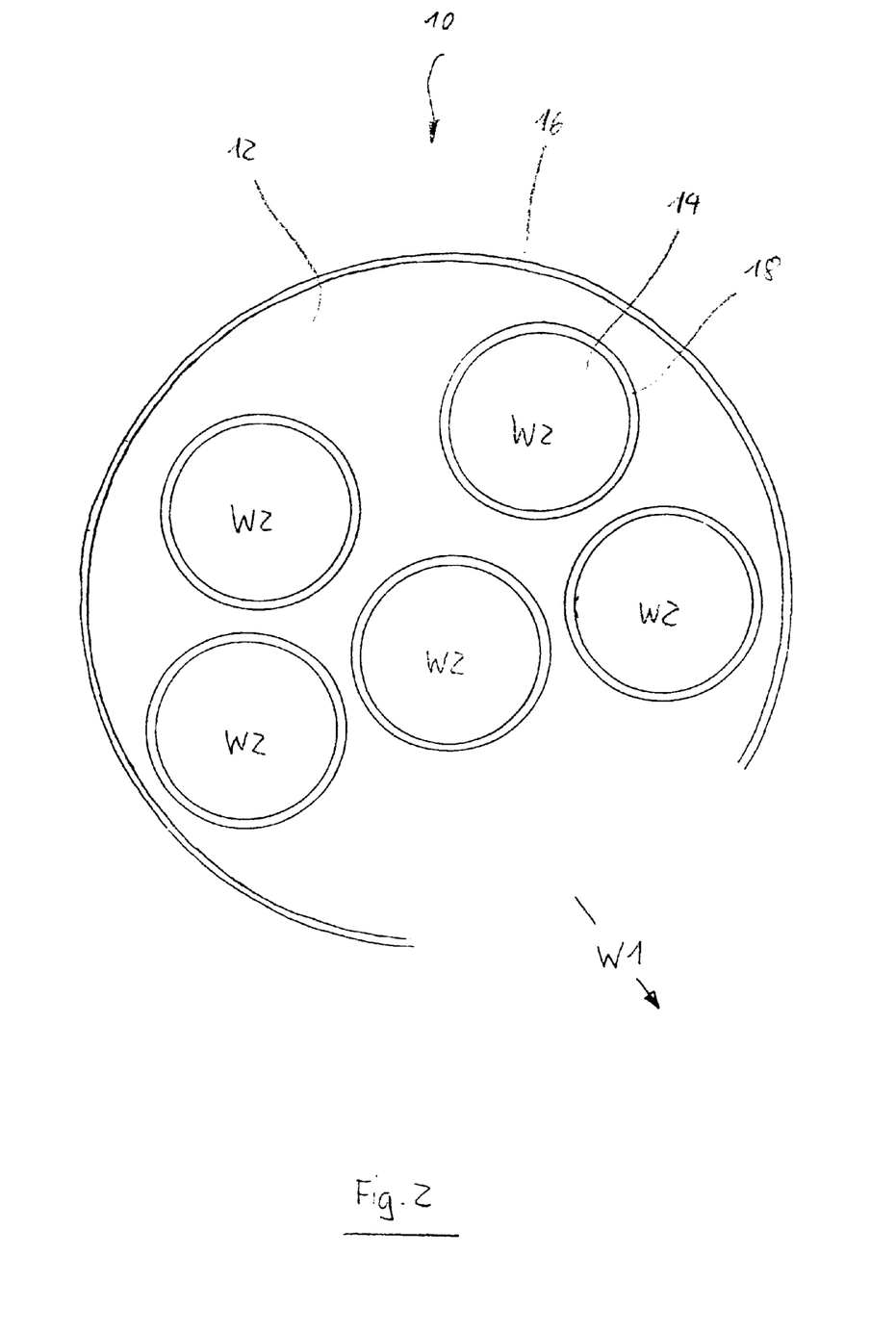
FIG. 2: is a view similar to FIG. 1 after bursting open of the microcapsules of an outer encapsulation layer of the first exemplary embodiment.
Figure 3:
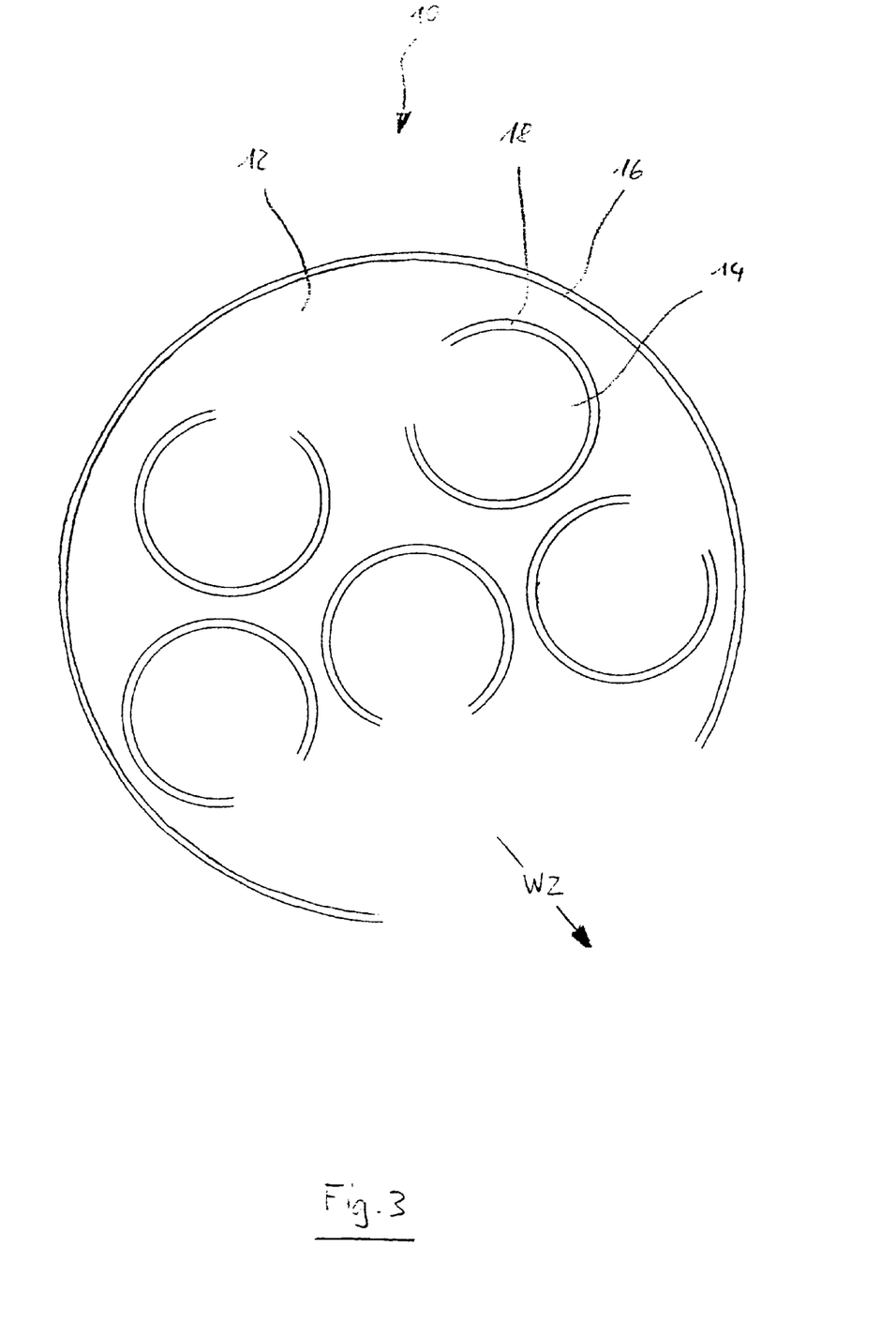
FIG. 3: is a view similar to FIG. 2 after bursting open of the microcapsules of an inner encapsulation layer of the first exemplary embodiment.

In FIG. 1, a microcapsule system bears the overall reference numeral 10. It comprises a plurality of outer capsules 12 of an outer encapsulation layer, only one of which is illustrated in FIGS. 1 to 3, however. This is designated as outer capsule 12, for the sake of simplicity.

The outer capsule 12 contains an active agent W1, and a plurality of capsules 14 of an inner encapsulation layer. These contain an active agent W2 and are known hereinafter as inner capsules 14.

The capsules 12 and 14 are each surrounded by a very thin capsule wall 16 and 18 respectively, which comprises an environment-induced material. In the present exemplary embodiment, this means that the outer capsule wall 16 bursts open under the influence, lasting for a certain period, of a temperature at the level of human body temperature, whereas the material of the capsule wall 18 of the inner capsules 14 comprises a material, which breaks down under the action, of longer duration, of human sweat and thus allows the capsules 14 to burst open.

In the present exemplary embodiment, the active agent W1 is a relatively mild chemical substance which reacts with human sweat to neutralize it. Active agent W2 is a similar substance which is more highly concentrated, however, and is thus more effective.

The microcapsule system 10 may be applied to a cloth with a binder in the manner described in DE 40 00 920 A1. Alternatively, the microcapsule system 10 may also be suspended in an emulsion, which is applied directly to the appropriate points on human skin.

As is clear from FIG. 2, the capsule wall 16 of the outer capsule 12 bursts first of all under the influence of body temperature, whereby the active agent W1 and the inner capsules 14 are released. The active agent thus reaches the skin of the user directly and may prevent the breakdown of sweat present there and stop further sweat formation. However, if, for example, after a relatively long period of heavy physical activity, a large amount of sweat is exuded, which can no longer be adequately combated by active agent W1, the capsule wall 18 of the inner capsules 14 is broken down under the action of this additional amount of sweat, thereby releasing the more effective active agent W2. This allows a need-oriented sequential release of active agents W1 and W2, which display different levels of efficacy.

Reference will now be made to the second exemplary embodiment of a microcapsule system 10 illustrated in FIGS. 4 to 9. Functionally equivalent elements are provided therein with the same reference numerals as in the exemplary embodiment illustrated in FIGS. 1 to 3. The following discussion will, moreover, concentrate in particular on the differences with regard to the first exemplary embodiment.

The microcapsule system 10 illustrated in FIGS. 4 to 9 has a three-layer structure and serves to produce a layer comprising a pressure-activatable multi-component adhesive.

The microcapsule system 10 again comprises a plurality of capsules 12 of an outer encapsulation layer, which comprise a thin and relatively porous, gas-permeable capsule wall 16. FIGS. 4 to 8 show only one of the capsules 12 of the outer encapsulation layer. For the sake of simplicity, this is known hereinafter as outer capsule 12.

Figure 4:
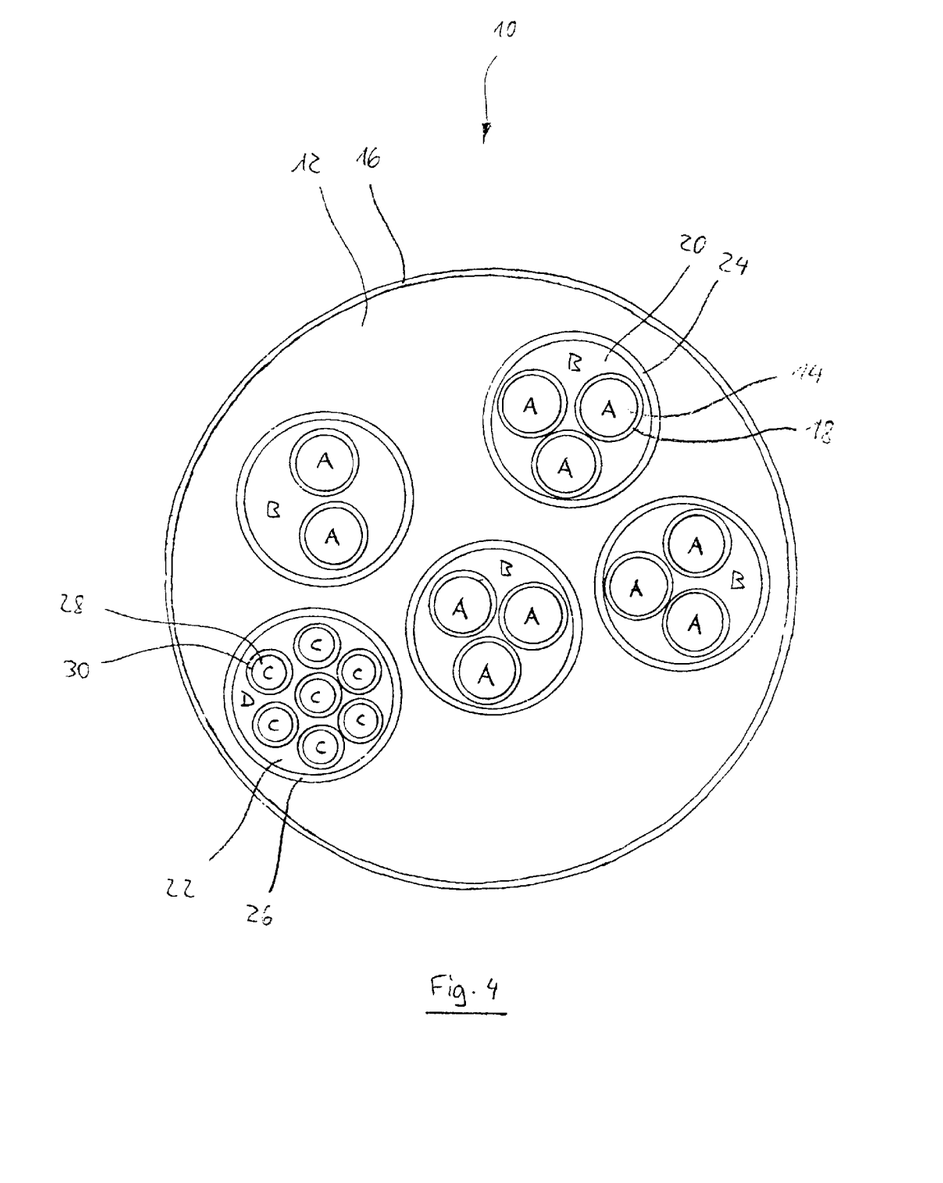
FIG. 4: shows a greatly enlarged section through a second exemplary embodiment of a microcapsule system.

This outer capsule 12 encloses a plurality of capsules 20 and 22 of a middle encapsulation layer, which are each surrounded by a thin capsule wall 24 and 26 respectively and are designated below as middle capsules 20 and 22. The middle capsules 20 in turn contain an active agent B, in this case hollow microspheres, which, in the final adhesive, serve as a filler, which is useful for example in filling unevennesses in the surfaces to be adhered, together with inner capsules 14 having a capsule capsule wall 18, containing an active agent, namely epoxy resin A. The capsules 14 of the inner encapsulation layer are designated hereinafter as inner capsules 14. The middle capsules 22 contain as active agent D a curing accelerator together with capsules 28 of a further inner encapsulation layer, which contain a curing agent as active agent C and comprise a thin capsule wall 30.

The materials of the capsule walls 16, 18, 24, 26 and 30 are environment-induced in the following manner: the capsule wall 16 of the outer capsule 12 breaks down under heat, more precisely at a temperature above 40° C. The capsule walls 24, 26 and 30 of the middle capsules 20 and 22 and the inner capsules 28 respectively break down under the influence of the active agent mixture AB, i.e. the epoxy resin/hollow microsphere mixture. The capsule walls 18 of the inner capsules 14 burst under mechanical load, i.e. under pressure or deformation for instance.

The mode of operation of the microcapsule system 10 illustrated in FIGS. 4 to 9 will now be described with reference to the example of application illustrated in FIG. 10.

First of all, the outer microcapsules 12 of the microcapsule system 10 are applied with a binder layer 32 to an appropriate surface 34 of a workpiece 36. The microcapsules 12 are then covered by a soft, impact-repellent film 38. In this state, the workpiece may be stored with the microcapsule system 10 for a relatively long period, without the adhesive layer becoming active and without breakdown of the individual components from which the adhesive layer is made.

Figure 5:
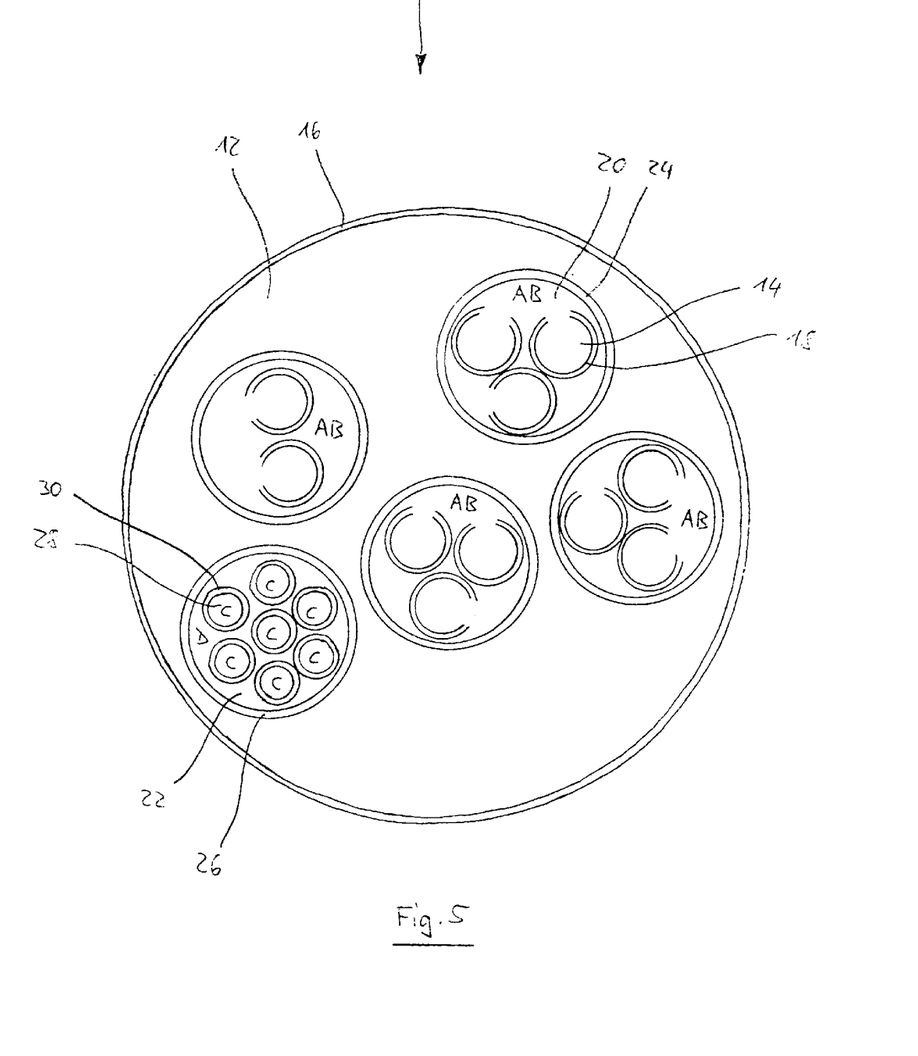
FIG. 5: is a view similar to FIG. 4 after bursting open of the microcapsules of an inner encapsulation layer of the second exemplary embodiment.
Figure 10:
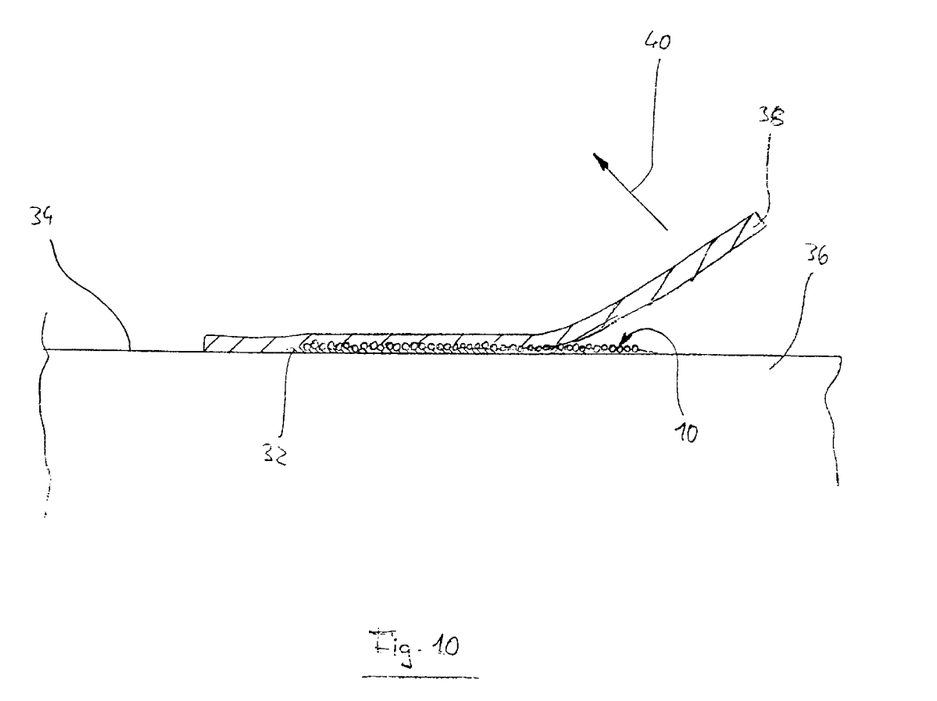
FIG. 10: shows a section through an example of application of the microcapsule system of FIGS. 4 to 9.

To activate the adhesive layer, i.e. to trigger the release sequence of the active agents A, B, C and D contained in the microcapsules 12, 16, 20, 22 and 28, the film 38 is peeled off, as indicated in FIG. 10 by the arrow 40. The workpiece 36 with the layer consisting of the microcapsule system 10 is then pressed against the wall to which it is to be adhered. In this way, the capsule walls 18 of the inner capsules 14 containing the epoxy resin A are deformed, thereby bursting and releasing the epoxy resin A. In this way, the hollow microspheres B and the epoxy resin A mix together inside the middle capsules 20. This is illustrated in FIG. 5.

Figure 6:
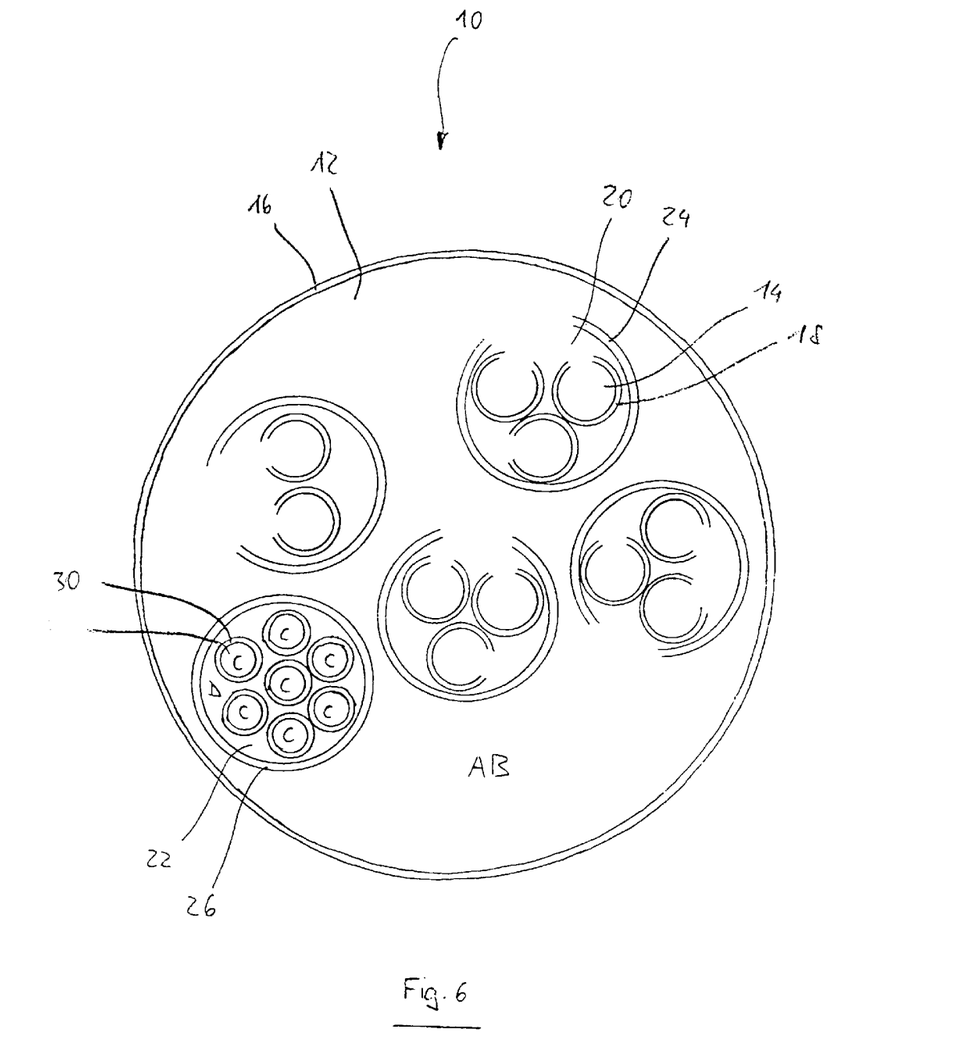
FIG. 6: is a view similar to FIG. 5 after bursting open of the microcapsules of a middle encapsulation layer of the second exemplary embodiment.

Since the capsule walls 24 of the middle capsules 20 are unstable with regard the epoxy resin A, these also burst, such that the mixture of hollow microspheres B and epoxy resin A reach the interior of the outer capsule 12 (c.f. FIG. 6).

Figure 7:
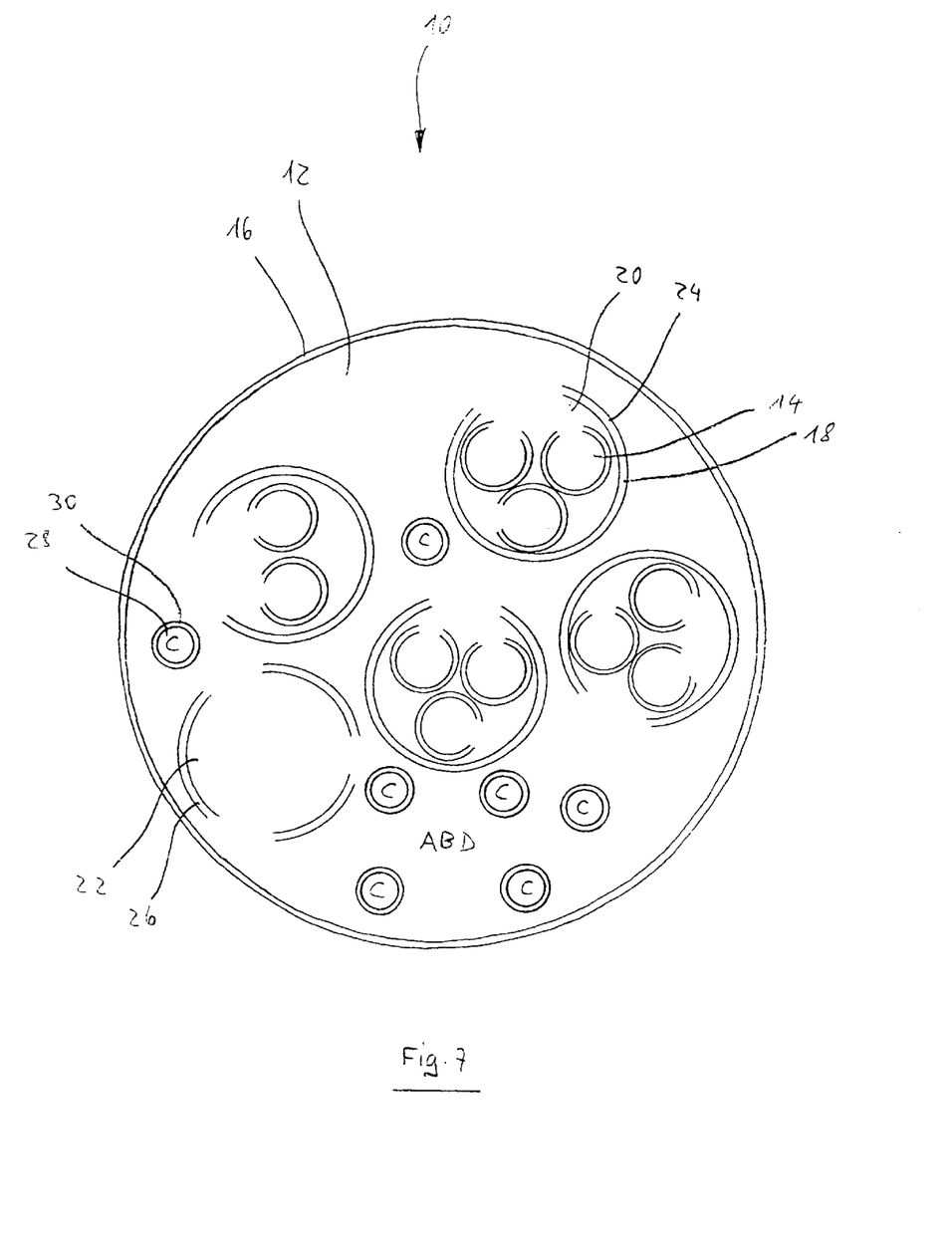
FIG. 7: is a view similar to FIG. 6 after bursting open of the microcapsules of all the middle encapsulation layers of the second exemplary embodiment.

The capsule wall 26 of the middle capsule 22 then also comes into contact with the epoxy resin A, thereby disintegrating and, in addition to the hollow microsphere/epoxy resin mixture AB, the curing accelerator D and the capsules 28 containing the curing agent C also spread out inside the outer capsules 12 (c.f FIG. 7).

Figure 8:
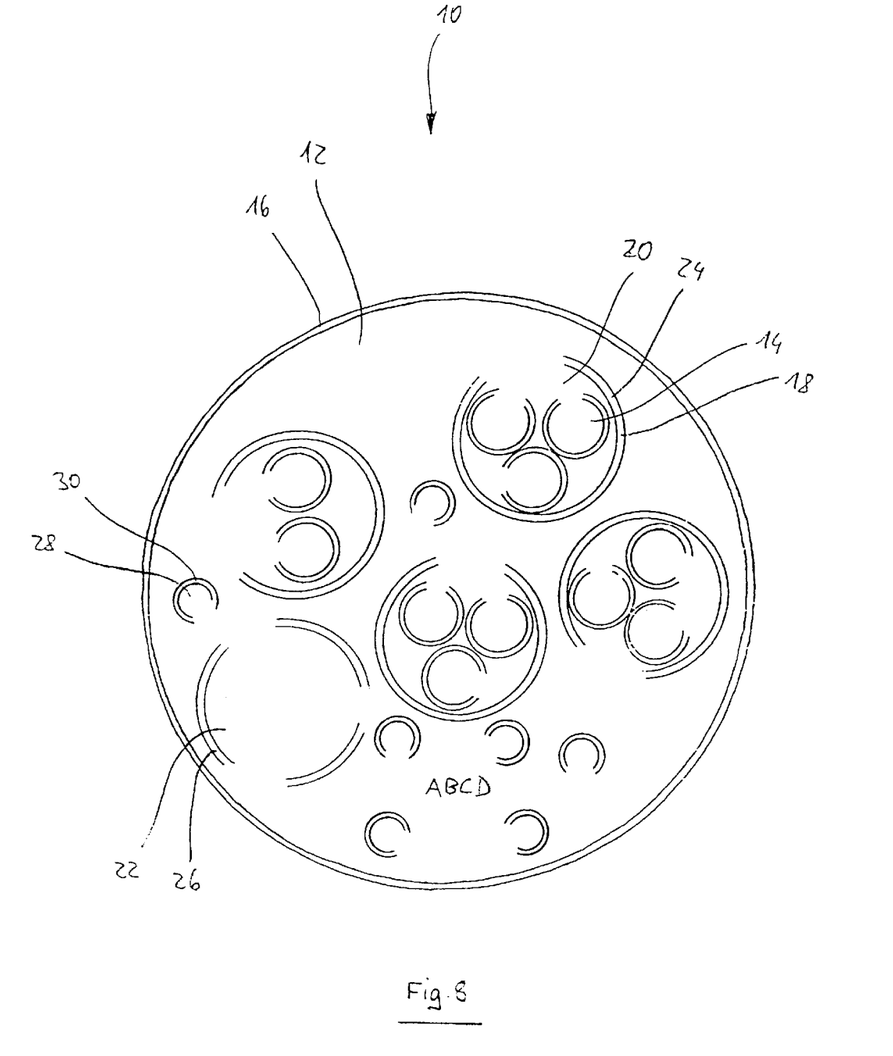
FIG. 8: is a view similar to FIG. 7 after bursting open of the microcapsules of a further inner encapsulation layer of the second exemplary embodiment.

Since, however, the capsule wall 30 thereof is likewise unstable with regard to the hollow microsphere/epoxy resin mixture AB, said wall disintegrates, such that finally the four substances hollow microspheres B, epoxy resin A, curing agent C and curing accelerator D are present inside the outer capsule 12 in a mixed state (c.f FIG. 8).

Figure 9:
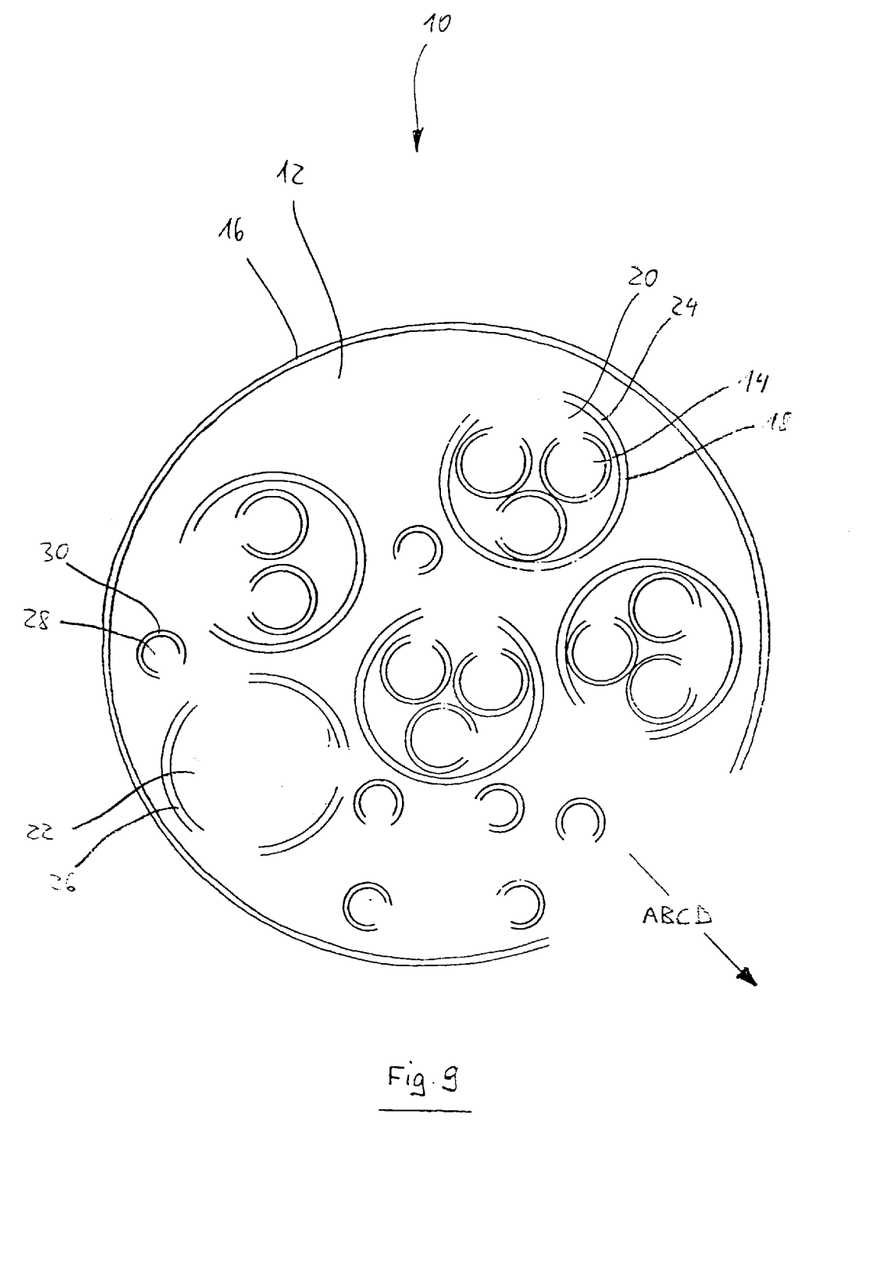
FIG. 9: is a view similar to FIG. 8 after bursting open of the microcapsules of the outermost encapsulation layer of the second exemplary embodiment.

In the case of the selection of components under consideration, this causes an exothermic reaction, which leads to an increase in temperature, which opens the capsule wall 16 of the outer capsules 12, such that the now ready-mixed multi-component epoxy resin adhesive is present in the form of a reacting and setting continuous adhesive layer (c.f FIG. 9).

A microcapsule system 10 constituted in this way may thus produce a high-strength multi-component adhesive, the individual components of which are initially separate from one another and may therefore be stored for a relatively long period. Through the simple application of pressure, the release sequence of the microcapsule system 10 is triggered, whereby the individual components of the multi-component adhesive are mixed together and the adhesive is activated.

The present multi-layer microencapsulation may naturally also be used in other sectors, for example for the sequential release of aromatic substances, drugs, lubricants or even fertilizers or pesticides.

Mention is made above of capsule walls bursting in response to environmental factors. It goes without saying that more gentle, incomplete opening of the capsules is feasible. All that is important is that the permeability of a capsule wall with regard to the capsule contents changes through the action of an environmental parameter.

What is claimed is:

1. A microcapsule system for environment-induced release of active agents, comprising:

a plurality of innermost microcapsules, which together comprise an innermost encapsulation layer, the innermost microcapsules having an innermost capsule wall comprising an environment-responsive material, wherein at least some of the innermost microcapsules contain an active agent;

one or more intermediate microcapsules, which together comprise an intermediate encapsulation layer, the intermediate microcapsules having an intermediate capsule wall comprising an environment-responsive material, wherein at least one of the one or more intermediate microcapsules accommodates two or more of the plurality of innermost microcapsules; and at least one outer microcapsule, comprising an outer encapsulation layer, the outer microcapsule having an outer capsule wall comprising an environment-responsive material, wherein the one or more intermediate microcapsules are accommodated in the outer microcapsule.

2. A microcapsule system as claimed in claim 1, wherein more than two encapsulation layers are provided.

3. A microcapsule system as claimed in claim 1, wherein the walls of the capsules of one encapsulation layer comprise the same environment-induced properties.

4. A microcapsule system as claimed in claim 1, wherein the walls of the capsules of one encapsulation layer comprise different environment-responsive properties.

5. A microcapsule system as claimed in claim 1, wherein the walls of the capsules of one encapsulation layer comprise different environment-induced properties from those of capsules of a different encapsulation layer.

6. A microcapsule system as claimed in claim 1, wherein at least one of the outer capsules and the intermediate capsules additionally include an active agent, and wherein the capsules of one encapsulation layer contain a different active agent from the capsules of a different encapsulation layer.

7. A microcapsule system as claimed in claim 1, wherein, from the point of view of time, walls of capsules of the outer encapsulation layer break open before walls of capsules of at least one of the innermost encapsulation layer and the intermediate encapsulation layer.

8. A microcapsule system as claimed in claim 5, wherein, from the point of view of time, walls of capsules of the innermost encapsulation layer break open before walls of capsules of at least one of the intermediate encapsulation layer and the outer encapsulation layer.

* * * * *